United States Patent
Wu et al.

(10) Patent No.: US 6,704,109 B2
(45) Date of Patent: Mar. 9, 2004

(54) DOWNHOLE FLUORESCENCE DETECTION APPARATUS

(75) Inventors: Xu Wu, Beijing (CN); Marian Faur, Massy (FR); Fabien Cens, Massy (FR); Jacques Sellin, Boissise le Roi (FR); Felix Chen, Newtown, CT (US); Oliver C. Mullins, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/055,654

(22) Filed: Jan. 23, 2002

(65) Prior Publication Data

US 2002/0118905 A1 Aug. 29, 2002

Related U.S. Application Data

(60) Provisional application No. 60/263,531, filed on Jan. 23, 2001.

(51) Int. Cl.[7] .................. G01N 33/28; G01N 21/25; G01V 5/00
(52) U.S. Cl. .................. 356/417; 356/436; 356/70; 250/253
(58) Field of Search .................. 356/417, 70, 436, 356/73, 440; 250/253, 255, 265, 268; 385/33, 12, 13

(56) References Cited

U.S. PATENT DOCUMENTS

| 2,334,475 | A | * | 11/1943 | Claudet ............... 250/268 |
|---|---|---|---|---|
| 5,430,813 | A | * | 7/1995 | Anderson et al. ............ 385/12 |
| 5,604,582 | A | * | 2/1997 | Rhoads et al. ............... 356/73 |
| 5,831,743 | A | | 11/1998 | Ramos et al. ............... 356/445 |
| 5,918,190 | A | * | 6/1999 | Nadeau ...................... 702/27 |
| 5,956,132 | A | | 9/1999 | Donzier ..................... 356/133 |
| 6,016,191 | A | | 1/2000 | Ramos et al. ................ 356/70 |
| 6,023,340 | A | | 2/2000 | Wu et al. ................... 356/432 |
| 6,075,611 | A | | 6/2000 | Dussan V. et al. .......... 356/432 |
| 6,124,597 | A | * | 9/2000 | Shehada et al. ......... 250/461.2 |
| 6,263,133 | B1 | * | 7/2001 | Hamm ....................... 385/33 |

* cited by examiner

Primary Examiner—Zandra V. Smith
(74) Attorney, Agent, or Firm—David P. Gordon; William B. Batzer; John J. Ryberg

(57) ABSTRACT

A downhole optical apparatus includes an LED source, reflectance and fluorescence detectors, a plurality of fibers, a dichroic mirror (DM), a beam splitter/coupler, a probe, a short-pass filter (SP), a dichroic long-pass filter (LP), and a lens. Source light filtered by the SP is fed to the DM which deflects light of desired wavelengths only. The deflected light is focused by the lens onto a fiber and is ultimately injected into an oil flow by the probe. Light reflected by oil or fluorescing therefrom is received by the probe, and split by the splitter. A small portion is received by the reflectance detector. A large portion is received by the lens and directed to the DM which deflects reflected light and passes light at longer fluorescing wavelengths. Passed light is further filtered by the DM and LP to eliminate remnants of the reflected light, and provided to the fluorescence detector.

22 Claims, 3 Drawing Sheets

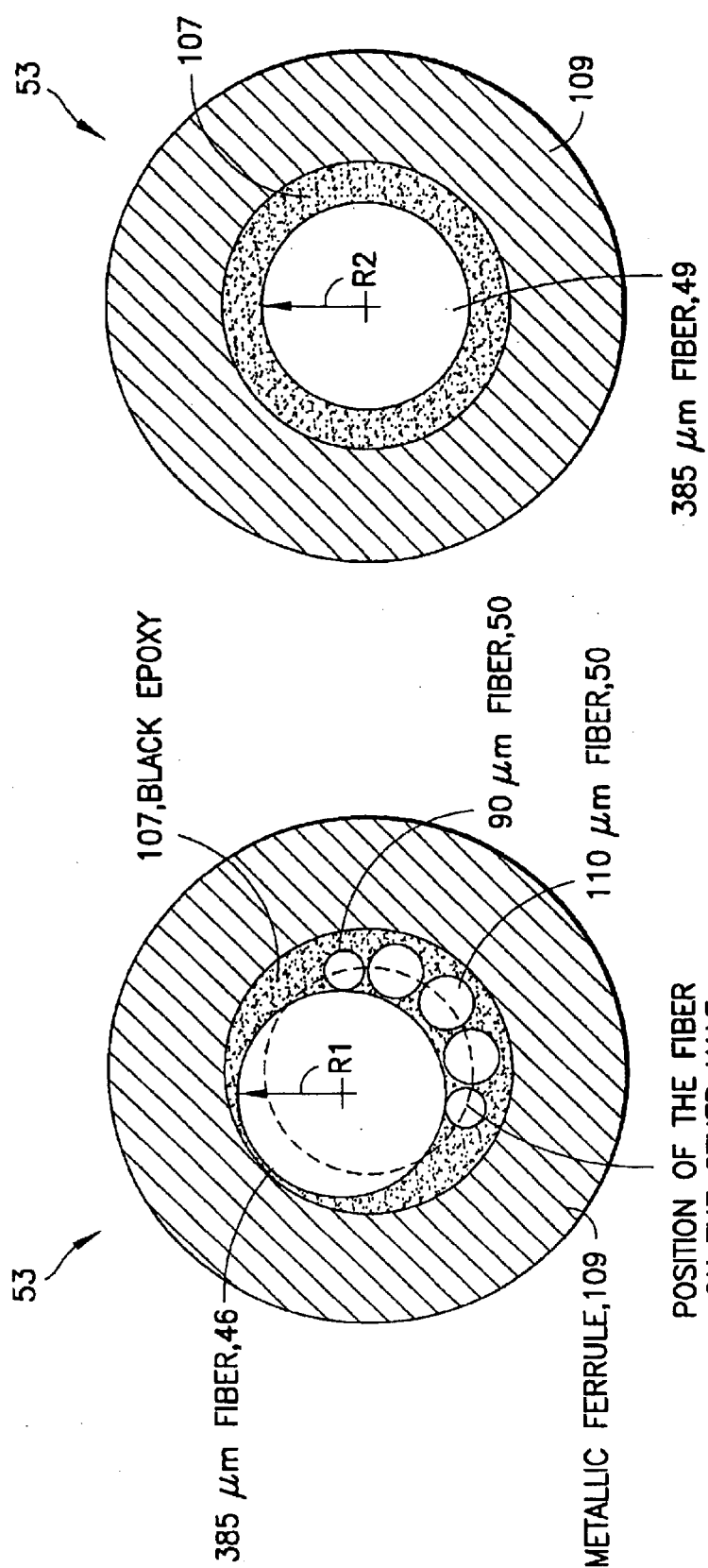

DOWNHOLE FLUORESCENCE DETECTION APPARATUS

This application claims priority from provisional patent application Ser. No. 60/263,531 filed Jan. 23, 2001.

This application is related to co-owned U.S. Pat. No. 5,831,743 entitled "Optical Probes", U.S. Pat. No. 6,016,191 entitled "Apparatus and Tool Using Tracers and Single Point Optical Probes for Measuring Characteristics of Fluid Flow in a Hydrocarbon Well and Methods of Processing Resulting Signals", U.S. Pat. No. 6,023,340 entitled "Single Point Optical Probe for Measuring Three-Phase Characteristics of Fluid Flow in a Hydrocarbon Well", and U.S. Pat. No. 6,075,611 entitled "Methods and Apparatus Utilizing a Derivative of a Fluorescence Signal for Measuring the Characteristics of a Multiphase Fluid Flow in a Hydrocarbon Well", all of which are hereby incorporated by reference herein in their entireties.

This application is also related to co-owned, concurrently filed U.S. Ser. No. 10/055,070 entitled "Apparatus and Methods for Determining Velocity of Oil in a Flow Stream" and U.S. Ser. No. 10/055,420 entitled "Optical Probes and Probe Systems for Monitoring Fluid Flow in a Well", both of which are hereby incorporated by reference herein in their entireties.

BACKGROUND OF THE INVENTION

1. Field of the Invention

The present invention relates to oil well optical apparatus. The present invention more particularly relates to optical apparatus for generating and detecting fluorescence in oil flowing in a well.

2. State of the Art

The use of optical systems for the analysis of fluids is well known. For example, as set forth in the patents incorporated by reference above, optical probes can be used downhole for measuring oil, water, and gas holdup in three-phase flows. In particular, light of excitation is coupled to a small optical probe that is deployed into a sample flow. Depending on the optical properties of the fluid surrounding the probe, the returning signal carries the optical signature of the fluid. Gas will induce a large reflectance, compared with liquids, due to the large mismatch of the index of refraction. Crude oils, on the other hand, will produce fluorescence under illumination. By analyzing both the reflectance and the fluorescence signals, the nature of the fluid in contact with the probe can be identified.

While the previously incorporated patents represent a major step forward in downhole analysis of fluids, the apparatus described therein are not as robust in certain circumstances as might be desired. For example, when borehole temperatures reach 200° C., many semiconductor lasers stop working. The low efficiency of energy conversion and light coupling of incandescent light sources makes them difficult to use. In addition, it is very difficult to detect the fluorescence of oil in the well because the fluorescence yield (i.e., the ratio of fluorescence signal to the corresponding excitation power) of crude oils is extremely low. For source excitation at 470 nm, the fluorescence yield is typically around 10e–4 for medium density crude oils. Further, the ratio of the received fluorescence signal to the received reflected signal is very small; i.e., the reflected signal can overwhelm the fluorescence signal. Moreover, where the optical system is to be located downhole, the tight space available permits only compact optics.

SUMMARY OF THE INVENTION

It is therefore an object of the invention to provide a downhole apparatus that enables a simultaneous detection of fluorescence and reflectance from a single fiber probe.

It is another object of the invention to provide apparatus that are reliable at high temperatures and that permit detection of oil fluorescence downhole.

It is a further object of the invention to provide downhole apparatus that maximize signal sensitivity and reduce noise in the detection of oil fluorescence.

In accord with the objects of the invention, the optical apparatus of the invention includes, among other things, a light emitting diode (LED) light source, a reflectance detector, a fluorescence detector, first, second, and third optics, a dichroic mirror, a beam splitter/coupler, a probe, a short pass filter, a dichroic long pass filter, and a lens. Source light from the LED is filtered by the short pass filter and fed to the dichroic mirror which deflects light of desired wavelength and passes light of undesired longer wavelengths. The deflected light is focused by the lens onto the first optic which is coupled to a second optic by the splitter coupler. The second optic is coupled to the probe which is placed in and injects light into the fluid flow. Light reflected by the fluid flow or fluorescing therefrom is received by the probe, and provided to the splitter/coupler by the second optic. The splitter/coupler forwards a first portion of the light to the reflectance detector via the third fiber, and a second portion of the light via the first fiber to the lens. Light received by the lens is directed to the dichroic mirror which deflects reflected light (i.e., light at the LED wavelength), and passes light at longer wavelengths (i.e., wavelengths generated by fluorescence). The passed light is further filtered by the dichroic mirror to eliminate remnants of the reflected light, and provided to the fluorescence detector.

According to a preferred aspect of the invention, the beam splitter/coupler is preferably arranged to pass at least ninety percent of light received from the second fiber optic to the first fiber optic for fluorescence detection. According to another preferred aspect of the invention, the fiber optic splitter/coupler of the invention includes on a first side, a large core fiber and a plurality of small core fibers potted with a black epoxy in a metallic ferrule, and on a second side, a single large core fiber centered in the ferrule. Surfaces of both sides are polished, and an optical couplant is used to minimize insertion loss. The ferrule mechanically holds the sides together without use of a glue.

Additional objects and advantages of the invention will become apparent to those skilled in the art upon reference to the detailed description taken in conjunction with the provided figures.

BRIEF DESCRIPTION OF THE DRAWINGS

FIGS. 3a and 3b are diagrams of the fiber optic splitter/coupler of FIG. 2.

DETAILED DESCRIPTION OF THE PREFERRED EMBODIMENTS

For purposes of illustration, the invention will be described primarily with reference to a production logging tool. However, at the outset, it should be appreciated by those skilled in the art that the invention can be implemented as a permanent installation in a producing well.

Figure 1:
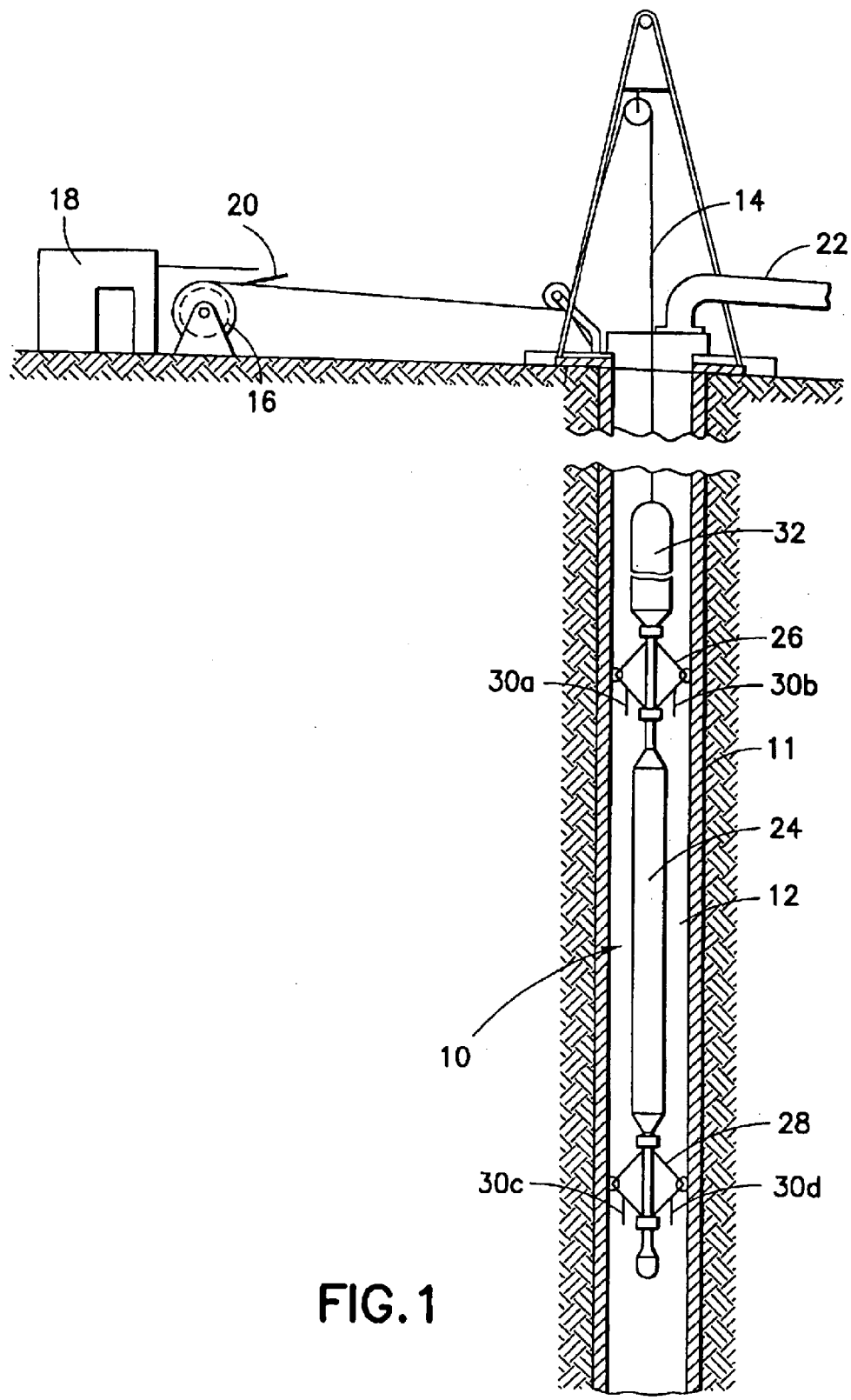
FIG. 1 is a schematic diagram of a production logging tool incorporating the optical apparatus of the invention and coupled to associated surface equipment.

Referring now to FIG. 1, a production logging tool 10 is suspended in a well 12 by means of a cable 14 which is coupled to a winch 16 for raising and lowering the tool 10. The cable 14 includes conductors (not shown) which may be either electrical or optical, or both, for communicating with data processing equipment 18 located on the surface. A cable displacement detector 20 is also provided at the surface in order to determine the depth of the tool 10 when it is lowered into the well 12. During production, fluid from the well is collected at the surface and conducted by a duct 22 to a storage or refining facility (not shown).

The tool 10 may take any of various forms such as disclosed in previously incorporated U.S. patents, or the previously incorporated concurrently filed applications. As shown in FIG. 1, the tool generally includes an elongate body 24 which is centered (or otherwise oriented) in the casing 11 of the well 12 by upper and lower bow springs 26, 28 (although only one set of bow springs is required for centering). The tool 10 is provided with a plurality of optical probes, e.g. 30a, 30b, 30c, 30d, which are located in the casing by the springs 26, 28. According to one embodiment of the invention, the optical source and detection equipment described hereinafter are located in the tool 10, e.g. in an upper electronics housing 32. The probes 30a–30d may take any of various formats as disclosed in the previously incorporated patents and related patent applications.

Figure 2:
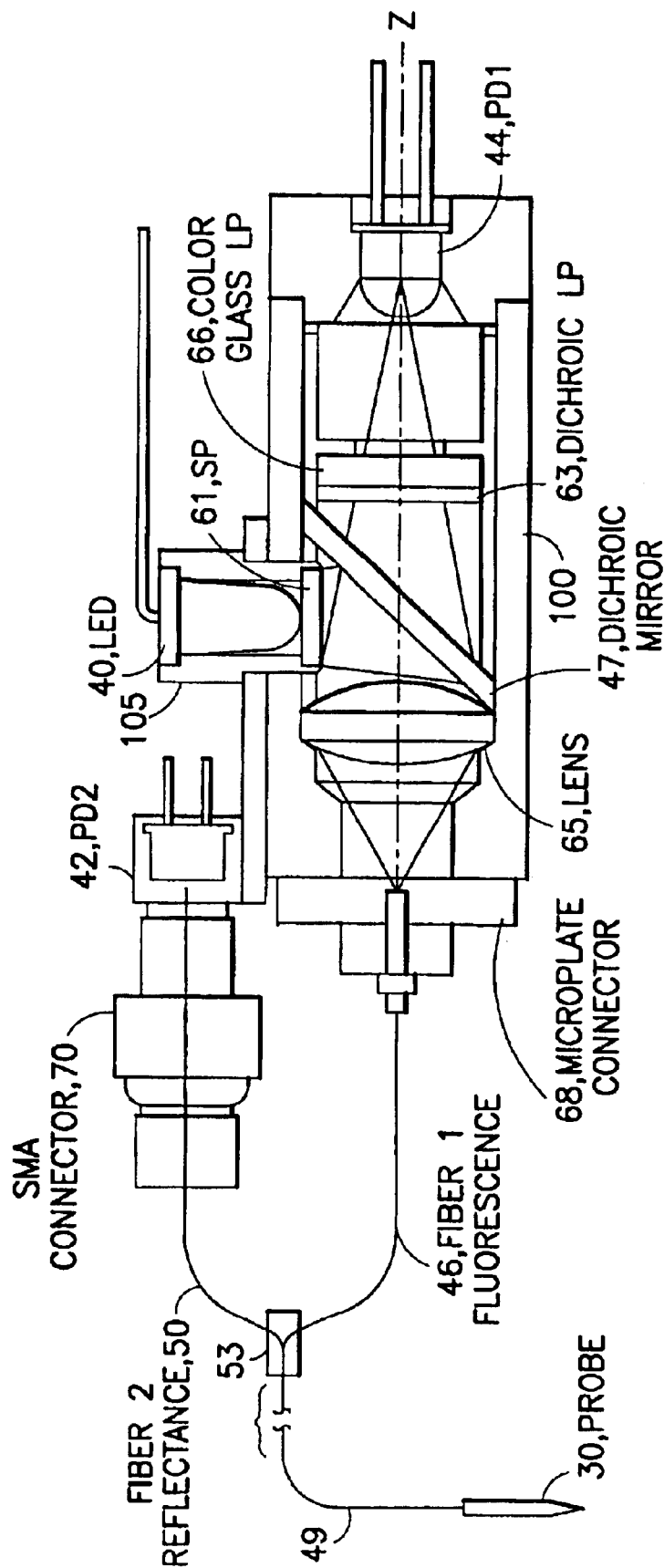
FIG. 2 is a schematic diagram of the apparatus of the invention.

Turning to FIG. 2, an arrangement of the probe, source and detectors is shown. According to the preferred embodiment, each optical probe (e.g., 30a) is optically coupled to a respective light source, reflectance detector, and fluorescence detector. The provided assembly of optical components enables a simultaneous detection of fluorescence and reflectance from a single fiber probe. The design maximizes signal sensitivity with a low noise figure. Tests have shown its reliable performance at high temperature. The preferred assembly includes, among other things, the probe 30, a light source 40, a reflectance detector 42, a fluorescence detector 44, a first fiber optic 46, a dichroic mirror 47, a fiber second optic 49, a third fiber optic 50, a beam splitter/coupler 53, a short pass filter 61, a dichroic long pass filter 63, and a lens 65. An optional colored glass long pass filter 66 may also be provided. The lens 65, dichroic mirror 47, light source 40, short pass filter 61, long pass filter 63, optional colored glass 66, and fluorescence detector 44 are all contained partially or completely in a housing or assembly box 100. The first fiber optic 46 is coupled to the housing via a microplate connector 68. The third fiber optic 50 is coupled to the reflectance detector 42 by a standard SMA connector 70. The fluorescence detector 44 is mounted to the housing.

The light source 40 is a light emitting diode (LED). LEDs are available in a broad range of wavelengths, from UV (375 nm) to near infrared, and in a variety of packaging. In the preferred embodiment, the LED is epoxy resin packaged with a light directivity (the emission half-angle) between seven and fifteen degrees, although LEDs in other packaging and with different light directivity may be used.

The short-pass filter 61 is an optical element that passes light below a certain wavelength (known as the filter edge) while rejecting light above that wavelength. The short-pass filter cuts off the tail emission of the source LED 40. The fluorescence of crude oils spreads over a range of wavelengths. The fluorescence is the strongest next to the excitation wavelength and decreases quickly as the wavelength moves away from it. The emission spectrum of an LED, on the other hand, exhibits a Gaussian distribution. Namely, its radiation extends to both sides of the center peak, and so will overlap with the fluorescence. Though the power intensity fades quickly, the tail of the source is still strong enough to overwhelm the usually feeble signal of fluorescence. To address this problem, the short-pass filter 61 is put in front of the LED to clean up the tail emission. The preferred short-pass filter has a steep transition in absorbance, from OD 0.1 to OD 4 in just a few tens of nanometers in wavelength. The edge of the filter (transition) is set next to the main emission of the source LED before the signal band starts. This cuts off the leakage of the tail emission effectively by four orders of magnitude (OD 4).

The dichroic mirror 47 reflects the main portion of the LED emission spectrum by ninety degrees, and the reflected light is focused with the lens 65 toward the entrance of a fiber optic 46. The reflection band of the mirror 47 is tailored according to the source wavelength; i.e. it reflects mainly the source emission but allows longer wavelength portion of the spectrum (fluorescence) coming back from the fiber optics to pass through. In this respect, it functions just like a long-pass filter (LP). Thus, both the source input and the signal paths are able to utilize the full cross-section of the fiber optics, helping achieve a high fluorescence signal level. The center of the edge of the dichroic mirror transmission (corresponding to the 50% transmission) is placed in the middle of those between the short-pass filter 61 and the long-pass filter 63.

Because the source excitation and the returning signals (reflectance and fluorescence) share the same optical path (i.e., fiber optic 49) at the probe, they have to be divided somewhere along the optical path. According to the preferred embodiment of the invention, a splitter 53 (also called a coupler, depending on which direction the light goes) is used to split the optical power from fiber 49 into two or more branches (fibers 46 and 50). Because the reflectance signal is two or three orders of magnitude stronger than the fluorescence signal, and the light directed to the reflectance detector is taken from the total, i.e., at the price of reducing the power injection and the fluorescence, in the preferred embodiment of the invention, splitter 53 is preferably arranged to provide at least ninety percent of the signal to the fluorescence detection optic 46 and at most ten percent to the reflectance detection optic 50. Details of a preferred splitter are seen in FIG. 3 discussed below.

In order to detect the very weak fluorescence signal, the reflected source light as well as the source scattering are preferably blocked out at the fluorescence detector 44. This is achieved by using the long-pass filter 63 in addition to the dichroic mirror 47 mentioned above. The long-pass filter 63 allows the transmission of wavelengths longer than the filter edge while rejecting those below it. Similar to the short-pass filter, the rejection/pass transition can occur in just several tens of nanometers from OD>4 to OD 0.1. According to the invention, the long-pass filter can be made of either a stack of dichroic layers or of color glass, or both. The spectral edges of the shortpass filter 61 and the long-pass filter 63 are preferably chosen to be as close as possible so as to maximize the signal. However, they should remain mutually exclusive in the pass band. The combined performance of absorbance (i.e., putting the two filters in series) is preferably not less than OD 4 throughout the range of interest.

The probe source and detector assembly functions as follows. Light from the LED 40 first passes through the short-pass filter 61 which cleans up the unwanted tail emission. The filtered light is then reflected forward by the dichroic mirror 47 (with longer wavelengths which escaped filtering passing through the mirror instead of being reflected). The reflected light is then focused by lens 65 onto fiber 46. Fiber 46 forwards the light to the splitter/coupler 53 which then passes onto the probe 30 via fiber 49.

Light reflected by or fluorescing from a fluid sample is carried by the probe 30 and fiber 49 back to the splitter/coupler 53. The splitter/coupler 53 forwards a portion of the light via fiber 50 and SMA connector 70 to the reflectance detector 42 and another portion (preferably 90% or more) to fiber 46. Light received by fiber 46 travels through the lens 65, and reaches the dichroic mirror 47. Because the fluorescence wavelengths are longer (i.e., they have undergone a red shift) than the reflected signal's wavelength, the fluorescence signal passes through the dichroic mirror, while the reflected light is again reflected by the dichroic mirror (toward the LED). The passed fluorescence signal is then received by the long-pass filter 63 and is converged onto the sensing area of fluorescence detector 44, which may be a photodiode. The long-pass filter 63 blocks the source scattering from entering the detector 44.

It should be noted that some color glass filters fluoresce. This means that while absorbing source scattering, the filter itself becomes a source of longer wavelengths. Thus, in accord with the preferred embodiment of the invention, a low fluorescent long-pass filter is utilized, or (as shown in FIG. 2) a dichroic long-pass filter is used in front of the color glass 66. Dichroic filters do not fluoresce.

Those skilled in the art will appreciate that the source power that can be delivered to the probe 30 depends in part on the alignment of optical components. Because of the fast nature of the optics (short focal length) and the small core size of the fiber, movements of a fractional millimeter can affect the power coupling result. In the preferred embodiment of the invention, the distances between the lens 65, the source LED 40, the dichroic mirror 47 and the terminal of the fiber 46 (in the microplate connector) are predetermined in a batch-top setup, and therefore only fine tunings are needed for an optimum coupling. On the source side, the plate 105 that houses the LED and short pass filter 61 can move slightly back and forth along the z direction (i.e., the LED axis). The LED itself can be rotated along its axis to compensate the asymmetry of the package. At the front of the assembly box 100, the microplate connector 68 is allowed a lateral movement in the x and y directions (i.e., in the plane perpendicular to the fiber optic 46) together with fiber optic 46. Finally, the end position of fiber 46 can be adjusted in the microplate connector 58 along the z direction (i.e., axis of the fiber 46) to achieve the maximum power. The fluorescence detector 44 is typically fixed as its position usually does not affect its performance. However, if needed a lens-type photodiode may be used to reduce its position sensitivity.

As will be appreciated by those skilled in the art, the fluorescence yield of crude oils is a function of the excitation wavelength. Generally, fluorescence yield increases as the excitation wavelength decreases. Furthermore, the high fluorescence yield in the shorter wavelengths of excitation is accompanied by a stronger absorbance in crude oils. Therefore, the fluorescence signal intensity per unit source power increases as the source color moves from red to blue. For a strong fluorescence signal, it is desirable to use a blue source. However, using a red source has its advantages. When oil passes through the probe, it often leaves a thin oil residue on the tip. Depending on the wettability of the probe, oil films can have a significant effect on the signal. They cause an unstable water signal level and sometimes even a false positive of the oil detection. These problems are aggravated with the blue source and dark oils due to the strong absorbance and high fluorescence yield. Using a red excitation minimizes these problems, because both factors decrease for a given oil film thickness. But the low oil film effect is at the price of a lower signal. For light crudes, oil films do not cause a problem; rather, the weak signal is the main concern. In short, the preferred color of the source excitation depends on the crude oil to be measured. If desired, the apparatus of the invention may be equipped with more than one LED/color of excitation, e.g., NSPB500S, a Nichia blue LED (peak wavelength 470 nm); NSPG500S, a Nichia green LED (peak wavelength 520 nm), a TLRH180P, a red LED made by Toshiba (peak 644 nm; a secondary emission peak at 870 nm). Other LEDs having other excitation wavelengths may also be incorporated into the apparatus.

As is discussed in detail in previously incorporated Ser. No. 10/055,420, the shape of the probe tip may also affect the fluorescence and reflection signals generated. To increase the fluorescence signal it is desirable to provide a probe with a small numerical aperture. Also, it should be appreciated that the probe should be designed so that it can be immersed in an abrasive fluid. It should therefore be made from an abrasive resistant material such as sapphire. However, sapphire, like certain color glass filters can fluoresce. Since other sources of fluorescence are undesirable as they add background noise and reduces the signal-to-noise ratio, it is desirable to reduce the fluorescence of the sapphire by annealing the probe in a hydrogen atmosphere at a temperature above 700° C.

Referring now to FIGS. 3a and 3b, details of mating sides of the preferred fiber optic splitter/coupler 53 of FIG. 2 are seen. As seen in FIG. 3a, a first side (i.e., the source and detector side) of the splitter includes the end of a large core fiber 46 and the ends of a plurality of laterally adjacent small core fibers (i.e., fiber 50) potted with a black epoxy 107 in a metallic ferrule 109. As seen in FIG. 3b, the second side of the splitter (i.e., the probe side) includes the end of a single large core fiber 49 centered in the ferrule 109 by a hole (not shown) in the ferrule and/or by black epoxy 107. The radius R2 of fiber 49 can be equal to or larger than the radius R1 of fiber 46 but preferably does not exceed what is necessary to cover the other smaller fibers 50; i.e., to provide enough light to the smaller fibers to enable reflectance detection. Since the reflectance signal is typically on the order of one thousand times the magnitude of the fluorescence signal, it will be appreciated that only a small portion of the smaller fibers 50 need to be covered by fiber 49 (e.g., thirty percent or less). In addition, the radius R2 of fiber 49 should not be smaller than radius of the probe 30 to which it is coupled. Surfaces of both sides are polished, and an optical couplant such as an optical gel is used between the ends of the fibers to minimize insertion loss. The ferrule mechanically holds the sides together without use of a glue.

In the preferred embodiment of the invention, the positioning of fiber 49 relative to fibers 46 and 50, and the radius of the cores of the large core fiber 46 and the plurality of small core fibers 50 are chosen such that at least ninety percent of the light carried by fiber 49 is directed to fiber 46; and only at most ten percent is forwarded to fiber 50. Thus, in one embodiment of the invention, fibers 46 and 49 are fibers having a 385 micron diameter, and fiber 50 is comprised of five fibers having diameters of between approximately 90 and 110 microns. With the fibers 46 and 50 in contact with each other, and fiber 49 exactly centered, all light from the source is forwarded from fiber 46 to fiber 49, and over ninety percent of the returning light is forwarded from fiber 49 to fiber 46. In this manner, a large percentage of the small fluorescence signal is forwarded to the fluorescence detector 44, while a sufficient ten percent or less of the much larger reflectance signal is forwarded to the reflectance detector 42.

There have been described and illustrated herein embodiments of a downhole fluorescence detection apparatus. While particular embodiments of the invention have been described, it is not intended that the invention be limited thereto, as it is intended that the invention be as broad in scope as the art will allow and that the specification be read likewise. Thus, while the invention was described with reference to a wellbore tool, it will be appreciated that stationary apparatus and/or plumbing can be utilized in or around the wellbore and may be cemented into place. Also, while the invention was described with reference to both a fluorescence and a reflectance detector, it will be appreciated that where only fluorescence information is desired, the reflectance detector, and hence the splitter and fiber optic coupled to the reflectance detect are not required. In addition, while certain fiber sizes were disclosed, it will be appreciated that other fiber sizes could be utilized. Further, while certain particular LED sources were described, other LED sources could be utilized. Also, while details of a preferred splitter/coupler were disclosed, other splitter/couplers could be utilized, or the preferred splitter/coupler could be modified; e.g., by using a dark epoxy which is colored other than black, by using fibers of different diameters, or by using different numbers of fibers. It will therefore be appreciated by those skilled in the art that yet other modifications could be made to the provided invention without deviating from its spirit and scope as claimed.

We claim:

1. An optical apparatus for investigating a fluid stream, comprising:
    a) an optical probe adapted to be inserted into the fluid stream;
    b) a light emitting diode (LED) light source which emits light at first wavelengths capable of causing natural fluorescence of the fluid stream at second wavelengths greater than said first wavelengths;
    c) a short pass filter adjacent said LED light source and adapted to block light at wavelengths greater than said first wavelengths;
    d) a dichroic mirror angled relative to said LED and adapted to reflect said light at said first wavelengths and to pass light at said wavelengths greater than said first wavelengths;
    e) a first optical fiber optically coupled to said optical probe;
    f) a lens adapted to focus light reflected by said dichroic mirror onto said first fiber optic, said lens being angled relative to said LED;
    g) a long pass filter adapted to block light at said first wavelengths, said long pass filter receiving and passing light at said second wavelengths received by said probe as a result of said natural fluorescence of the fluid stream; and
    h) a fluorescence detector which receives light passed by said long pass filter.

2. An optical apparatus according to claim 1, wherein:
    said dichroic mirror is angled approximately forty-five degrees relative to said LED and relative to said lens, and said lens is angled approximately ninety degrees relative to said LED.

3. An optical apparatus according to claim 1, further comprising:
    a housing surrounding at least a portion of said LED, said short pass filter said lens, said dichroic mirror and said long pass filter.

4. An optical apparatus according to claim 1, further comprising:
    an optical splitter/coupler connected to said first optical fiber;
    a second optical fiber connected to said optical splitter/coupler and to said probe;
    a third optical fiber connected to said optical splitter/coupler; and
    a reflectance detector coupled to said third optical fiber.

5. An optical apparatus according to claim 4, wherein:
    said reflectance detector and said fluorescence detector are both photodiodes.

6. An optical apparatus according to claim 4, wherein:
    said first optical fiber has a first diameter, and
    said third optical fiber comprises a plurality of optical elements having diameters smaller than said first diameter.

7. An optical apparatus according to claim 6, wherein:
    said second optical fiber has a second diameter at least as large as said first diameter.

8. An optical apparatus-according to claim 6, wherein:
    said optical splitter/coupler comprises a ferrule for receiving ends of said first optical fiber, said plurality of optical elements, and said second optical fiber, and dark epoxy which surrounds said end of said second optical fiber and envelops said ends of said first optical fiber and said ends of said plurality of optical elements.

9. An optical apparatus according to claim 1, wherein:
    said LED has a peak wavelength between approximately 470 nm and 644 nm inclusive.

10. An optical apparatus according to claim 1, wherein:
    said long pass filter comprises a dichroic long pass filter in conjunction with a color glass long pass filter.

11. An optical apparatus according to claim 1 wherein said fluid stream is in a well, and wherein:
    said optical apparatus is located on a logging tool suspended in the well.

12. An optical apparatus according to claim 8, wherein:
    said dark epoxy is black epoxy.

13. An optical apparatus according to claim 8, wherein:
    said second optical fiber is centered in said ferrule by said epoxy.

14. An optical apparatus according to claim 8, wherein:
    said first optical fiber has a diameter of approximately 385 microns, said second optical fiber has a diameter of approximately 385 microns, and said third optical elements have a diameter of between approximately 90 and approximately 110 microns.

15. An optical apparatus for investigating a fluid stream, comprising:
    a) an optical probe adapted to be inserted into the fluid stream;
    b) a light emitting diode (LED) light source which emits light at first wavelengths capable of causing natural fluorescence of the fluid stream at second wavelengths greater than said first wavelengths;
    c) a short pass filter adjacent adapted to block light at wavelengths greater than said first wavelengths;
    d) a dichroic mirror adapted to reflect said light at said first wavelengths and to pass light at said wavelengths greater than said first wavelengths;
    e) a first optical fiber optically coupled to said optical probe;

f) a lens adapted to focus light reflected by said dichroic mirror onto said first fiber optic;

g) a long pass filter adapted to block light at said first wavelengths and to pass light at said second wavelengths; and h) a fluorescence detector which detects light at said second wavelengths, wherein said LED, dichroic mirror, lens, short pass filter and long pass filter are arranged such that light emitted by said source is filtered by said short pass filter and said dichroic mirror whereby substantially no light of wavelengths greater than said first wavelengths is directed via said lens to said first fiber optic and to said probe, and whereby substantially no light of wavelengths less than said second wavelengths is passed through said dichroic mirror and long pass filter to said fluorescence detector.

16. An optical apparatus according to claim 15, wherein:

said dichroic mirror is angled approximately forty-five degrees relative to said LED and relative to said lens, and said lens is angled approximately ninety degrees relative to said LED.

17. An optical apparatus according to claim 15, further comprising:

a housing surrounding at least a portion of said LED, said short pass filter said lens, said dichroic mirror and said long pass filter.

18. An optical apparatus according to claim 15, further comprising:

an optical splitter/coupler connected to said first optical fiber;

a second optical fiber connected to said optical splitter/coupler and to said probe;

a third optical fiber connected to said optical splitter/coupler; and a reflectance detector coupled to said third optical fiber.

19. An optical apparatus according to claim 18, wherein:

said reflectance detector and said fluorescence detector are both photodiodes.

20. An optical apparatus according to claim 18, wherein:

said first optical fiber has a first diameter, said third optical fiber comprises a plurality of optical elements having diameters smaller than said first diameter, said second optical fiber has a second diameter at least as large as said first diameter, and said optical splitter/coupler comprises a ferrule for receiving ends of said first optical fiber, said plurality of optical elements, and said second optical fiber, and dark epoxy which surrounds said end of said second optical fiber and envelops said ends of said first optical fiber and said ends of said plurality of optical elements.

21. An optical apparatus according to claim 15, wherein:

said LED has a peak wavelength between approximately 470 nm and 644 nm inclusive, and said long pass filter comprises a dichroic long pass filter in conjunction with a color glass long pass filter.

22. An optical apparatus according to claim 15, wherein said fluid stream is in a well, and wherein:

said optical apparatus is located on a logging tool suspended in the well.

* * * * *